(12) United States Patent
Mangione (10) Patent No.: US 8,221,422 B2
(45) Date of Patent: Jul. 17, 2012

(54) DEVICE AND METHOD FOR SECTIONING A VERTEBRAL LAMINA

(75) Inventor: Paolo Mangione, Pessac (FR)

(73) Assignee: LDR Medical, Rosières Près Troyes (FR)

( * ) Notice: Subject to any disclaimer, the term of this patent is extended or adjusted under 35 U.S.C. 154(b) by 1313 days.

(21) Appl. No.: 10/575,065

(22) PCT Filed: Oct. 6, 2004

(86) PCT No.: PCT/IB2004/003244
§ 371 (c)(1), (2), (4) Date: May 30, 2006

(87) PCT Pub. No.: WO2005/034771
PCT Pub. Date: Apr. 21, 2005

(65) Prior Publication Data
US 2007/0149974 A1  Jun. 28, 2007

(30) Foreign Application Priority Data
Oct. 9, 2003  (FR) ...................... 03 11791

(51) Int. Cl.
A61B 17/00 (2006.01)
A61B 17/32 (2006.01)
A61B 17/34 (2006.01)
(52) U.S. Cl. ............. 606/79; 606/83; 606/167; 606/185
(58) Field of Classification Search ............. 606/79–84, 606/90, 167–173, 176, 178, 182, 184–186
See application file for complete search history.

(56) References Cited

U.S. PATENT DOCUMENTS

| 4,586,497 | A | * | 5/1986 | Dapra et al. | 606/80 |
| 5,273,519 | A | * | 12/1993 | Koros et al. | 606/83 |
| 5,383,888 | A | * | 1/1995 | Zvenyatsky et al. | 606/206 |
| 5,484,441 | A | * | 1/1996 | Koros et al. | 606/79 |
| 5,582,618 | A | * | 12/1996 | Chin et al. | 606/170 |

(Continued)

FOREIGN PATENT DOCUMENTS
FR  2860701 B1  1/2006
(Continued)

OTHER PUBLICATIONS

FR 2 860 701 Preliminary Search Report, National Institute of Industrial Property (France), May 25, 2004.

(Continued)

*Primary Examiner* — Thomas C. Barrett
*Assistant Examiner* — Matthew Lawson
(74) *Attorney, Agent, or Firm* — Denko Coburn & Lauff LLP (57) ABSTRACT

A device for sectioning a vertebral lamina, which can comprise a base for positioning the device and protecting the medullar canal when sectioning the lamina, sectioning means slide-mounted in the base along a first axis, a first piston slide-mounted in a sleeve of the sectioning means along a second axis secant to the first sliding axis of the sectioning means, a second piston made integral with the first piston and slide-mounted in the base along a third axis, the sectioning means being provided with a cutting element oriented in opposite direction to the second piston with respect to the sleeve, and the sliding of the second piston along the third axis causing the sliding of the sectioning means along the first axis via the first piston.

6 Claims, 6 Drawing Sheets

U.S. PATENT DOCUMENTS

| | | | |
|---|---|---|---|
| 5,620,453 A * | 4/1997 | Nallakrishnan | 606/166 |
| 5,620,456 A * | 4/1997 | Sauer et al. | 606/185 |
| 5,722,977 A | 3/1998 | Wilhelmy | |
| 5,908,432 A * | 6/1999 | Pan | 606/167 |
| 6,126,664 A * | 10/2000 | Troxell et al. | 606/84 |
| 6,258,094 B1 | 7/2001 | Nicholson et al. | |
| 6,261,293 B1 | 7/2001 | Nicholson et al. | |
| 6,610,089 B1 | 8/2003 | Liu et al. | |
| 6,663,636 B1 * | 12/2003 | Lin | 606/87 |
| 6,673,075 B2 | 1/2004 | Santilli | |
| 6,679,887 B2 | 1/2004 | Nicholson et al. | |
| 6,800,093 B2 | 10/2004 | Nicholson et al. | |
| 7,208,005 B2 * | 4/2007 | Frecker et al. | 606/205 |
| 2001/0034526 A1 * | 10/2001 | Kuslich et al. | 606/80 |
| 2003/0135218 A1 * | 7/2003 | Eckman | 606/79 |
| 2003/0171756 A1 * | 9/2003 | Fallin et al. | 606/80 |
| 2005/0038439 A1 * | 2/2005 | Eckman | 606/79 |
| 2008/0177265 A1 * | 7/2008 | Lechot | 606/79 |

FOREIGN PATENT DOCUMENTS

| | | |
|---|---|---|
| JP | 2002-282263 A | 10/2002 |
| JP | 2002282263 A | 10/2002 |
| WO | WO 2005034771 A1 | 4/2005 |

OTHER PUBLICATIONS

PCT/IB2004/003244 International Search Report, EPO, Mar. 24, 2005.

PCT/IB2004/003244 Written Opinion of the International Searching Report, EPO, Mar. 22, 2005.

PCT/IB2004/003244 International Preliminary Report of Patentability, WIPO, Apr. 10, 2006.

Laminotome de Mangione (website) 1 page, www.ldrmedical.fr/mobidisc.htm, Sep. 19, 2004.

* cited by examiner

DEVICE AND METHOD FOR SECTIONING A VERTEBRAL LAMINA

The present invention concerns a device and method for sectioning a vertebral lamina.

It is sometimes necessary to section a vertebral lamina to release the medullar canal, for example in patients with a narrow medullar canal. The vertebral lamina is then sectioned at two substantially symmetrical points with respect to the spinous process, located at either side of the latter.

In the prior art it is known to section a vertebral lamina using a Gauge forceps and a Kerisson rongeur used to cut through the lamina $mm^3$ by $mm^3$. However, this device, which is highly suitable for neurosurgery, is very restrictive in this case on account of the numerous operations to be conducted to section the lamina completely, leading to loss of time during surgery.

The purpose of the present invention is to overcome some of the disadvantages of the prior art by proposing a device for sectioning a vertebral lamina which is reliable and quick and easy to use.

This purpose is achieved with a device for sectioning a vertebral lamina, characterized in that it comprises a base for positioning the device and protecting the medullar canal when sectioning the lamina, sectioning means slide-mounted in the base along a first axis contained in the longitudinal plane of symmetry of the device, a first piston slide-mounted in a sleeve of the sectioning means along a second axis contained in the longitudinal plane of symmetry of the device and secant to the first sliding axis of the sectioning means, a second piston made integral with the first piston and slide-mounted in the base along a third axis contained in the longitudinal plane of symmetry of the device, the sectioning means being provided with a cutting element lying within the longitudinal plane of symmetry of the device, and oriented in opposite direction to the second piston with respect to the sleeve, and the sliding of the second piston along the third axis causing sliding of the sectioning means along the first axis via the first piston.

According to another feature, the second piston consists of a body provided, at one of its ends, with a ring into which the second piston engages, the ring being held on the piston by a screwhead, and at the other of its ends with a handle, said body being slide-mounted in a hollow tube of the base of the device and the handle being sized larger than the tube diameter to act as abutment to counter the weight effect of the second piston sliding within the tube.

According to another feature, the sectioning means are slide-mounted on a bottom part of the base, provided with a slide rail for the cutting element, the bottom part connecting first portions of two side faces of the base arranged facing one another, the longitudinal axis of said first portions being parallel to the first axis, second portions of the base side faces having their longitudinal axis parallel to the third axis.

According to another feature, the tube of the base is formed on the second portions of the side faces of the base.

According to another feature, the bottom part tapers towards a direction opposite the base tube and the first portions of the side faces are provided with a recess enabling the bottom part to be caused to slide between the lamina to be sectioned and the dura mater and acting as abutment for the device against the lamina of the said vertebra.

According to another feature, the end of the cutting element is bevelled to facilitate sectioning of the vertebral lamina.

A second purpose of the invention is to propose a method for sectioning a vertebral lamina using the sectioning device of the invention.

Other characteristics and advantages of the present invention will become more readily apparent on reading the description below given with reference to the appended drawings, in which.

The device for sectioning a vertebral lamina according to the invention, as shown in FIGS. 1 to 8, comprises a base 4 provided with a tongue 410 for positioning the device close to a vertebral lamina and for protecting the medullar canal when sectioning the lamina, and lamina sectioning means 1 is connected via a first piston 2, to a second piston 3, the sectioning means 1 and the second piston 3 being able to slide in the base 4 of the device.

Figure 3:
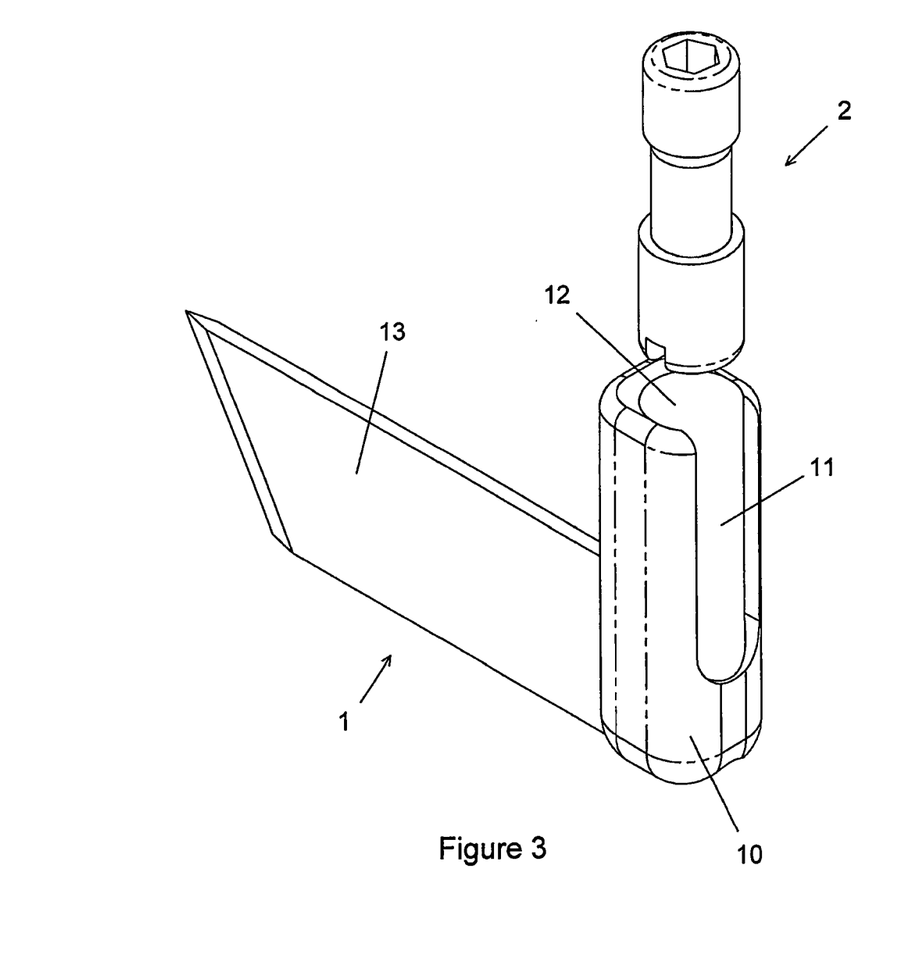
FIG. 3 is a perspective view of the sectioning means of the device according to the invention.

As shown in particular in FIG. 3, the sectioning means 1 comprise a sleeve 10 that is hollow and has a substantially vertical axis. This sleeve 10 comprises a first outward opening 11, called upper opening, made in its upper end and a second outward opening 12, called side opening, made in one of its sides at a determined height. The upper 11 and side 12 openings meet at the intersection between the upper end of the sleeve 10 and the side of the sleeve 10 comprising the side opening 12. A cutting element 13 positioned in a substantially vertical plane and along a substantially horizontal axis, is formed on the side opposite side opening 12. To facilitate sectioning of a vertebral lamina, the end of cutting element 13 opposite the sleeve 10 is bevelled.

The sleeve 10 of the sectioning means 1 is adapted to house the first piston 2, which can slide in said sleeve 10 parallel to the axis of the sleeve 10. The width of the side opening 12 being narrower than the largest diameter of the first piston 2, the first piston 2 is retained by the edges of the side opening 12 when it slides within the sleeve 10, preventing it from tilting about an axis perpendicular to the axis of the sleeve 10. On the other hand, the upper opening 11 of the sleeve 10 being of greater diameter than the largest diameter of the first piston 2, the first piston 2 can be removed from the sleeve 10 via the upper end of the sleeve.

Figure 4:
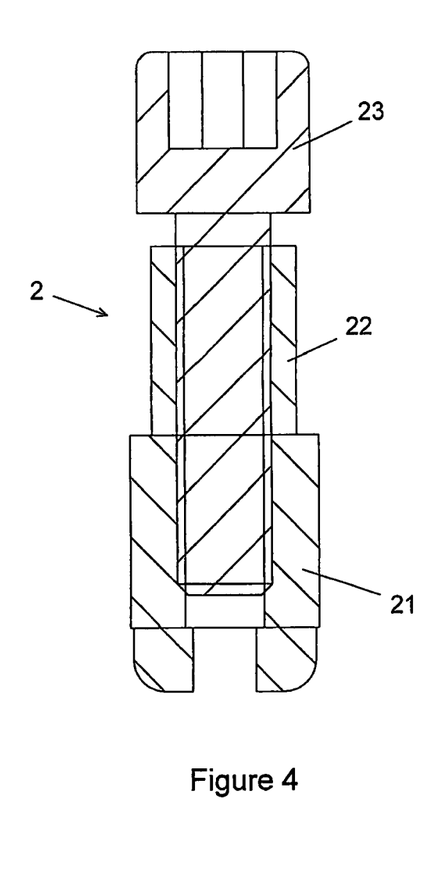
FIG. 4 is a cross-section view of the piston of the sectioning means of the device according to the invention, FIGS. 5 et 6 are an overhead view of the device according to the invention, the cutting element being respectively retracted and deployed.

The first piston 2 comprises a body 21, 22 threaded on the inside. The body of the first piston comprises two substantially cylindrical parts, of different diameters, positioned in the extension of one another and forming an integral part of one another. The diameter of the lower part 21 of the piston is the largest diameter which is greater than the width of the side opening 11 of the sleeve 10 of the sectioning means 1.

The upper part 22 of the body of the first piston 2 fits into a ring (33, FIG. 2) of the second piston 3. A screw 23, whose head has a diameter that is at least greater than the inner diameter of said ring 33, is screwed into the body 21, 22 of the first piston, so as to hold ring 33 around the upper part 22 of the body of the first piston 2, thereby maintaining the first and second pistons 2, 3 integral with one another.

The second piston 3 of the device according to the invention consists of a substantially cylindrical body 31 provided at one of its ends with a preferably flat handle 32 positioned in a plane perpendicular to the axis of the body 31 of the second piston, and at its other end with the ring 33 fitted onto the upper part 22 of the first piston 2.

The base 4 of the device according to the invention consists of two parts 41, 42, that are integral with one another.

Figure 5:
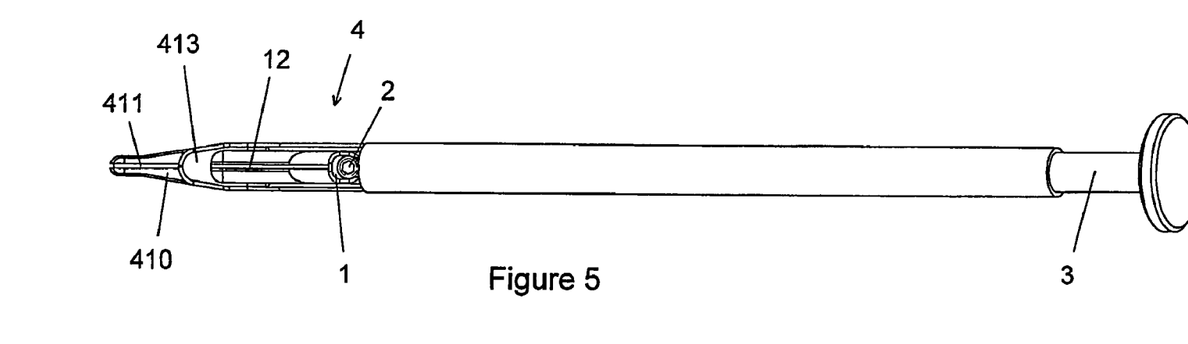
Figure 6:
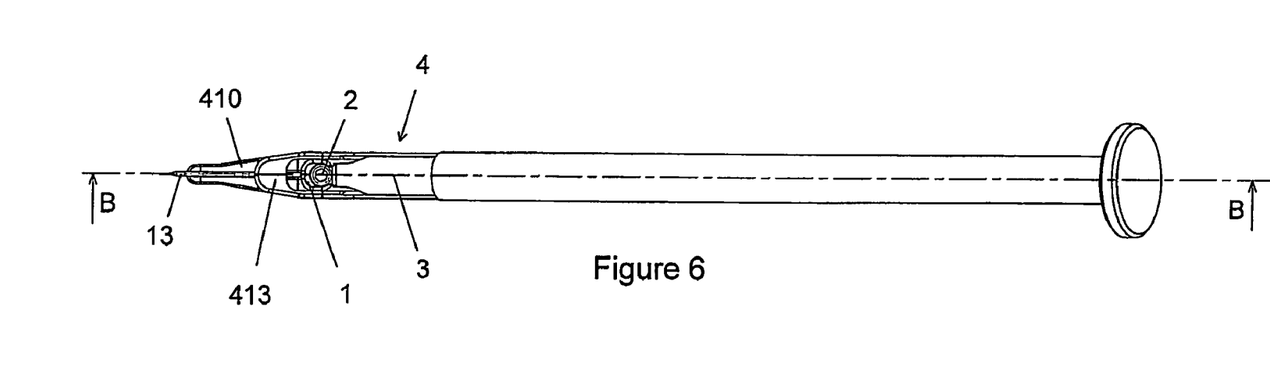

The first part 41 of the base 4 of the device according to the invention consists of a bottom part, which forms the tongue 410 for positioning the device close to a vertebral lamina and for protecting the medullar canal during lamina sectioning, and of two side faces. This first part 41 of the base 4 is intended to house the sectioning means. The bottom part 410 of the first part 41 of the base 4 of the device according to the invention is provided with a rail 411, in which the cutting element 13 of the sectioning means 1 lies and can slide. The two side faces face one another and each comprise two portions 412, 414 having respective longitudinal axes $A_1$ and $A_2$ forming an angle α between them. The bottom part 410 of the base 4 connects side face portions 412 with longitudinal axis $A_1$ over their entire length. These portions 412 with longitudinal axis $A_1$ gradually draw close to one another as they move away from the intersection between the two portions 412, 414 of the side faces. Therefore, as can be seen in FIGS. 5 and 6 in particular, the bottom part tapers towards what will be hereafter called the front of the device according to the invention.

The bottom part 410, intended to be inserted between the lamina to be sectioned and the dura mater, must both be sufficiently thin so as not to compress the medullar canal more than is necessary and sufficiently thick to protect the medullar canal during sectioning of the lamina.

Side face portions 414 with longitudinal axis $A_2$ are substantially parallel to one another.

Figure 1:
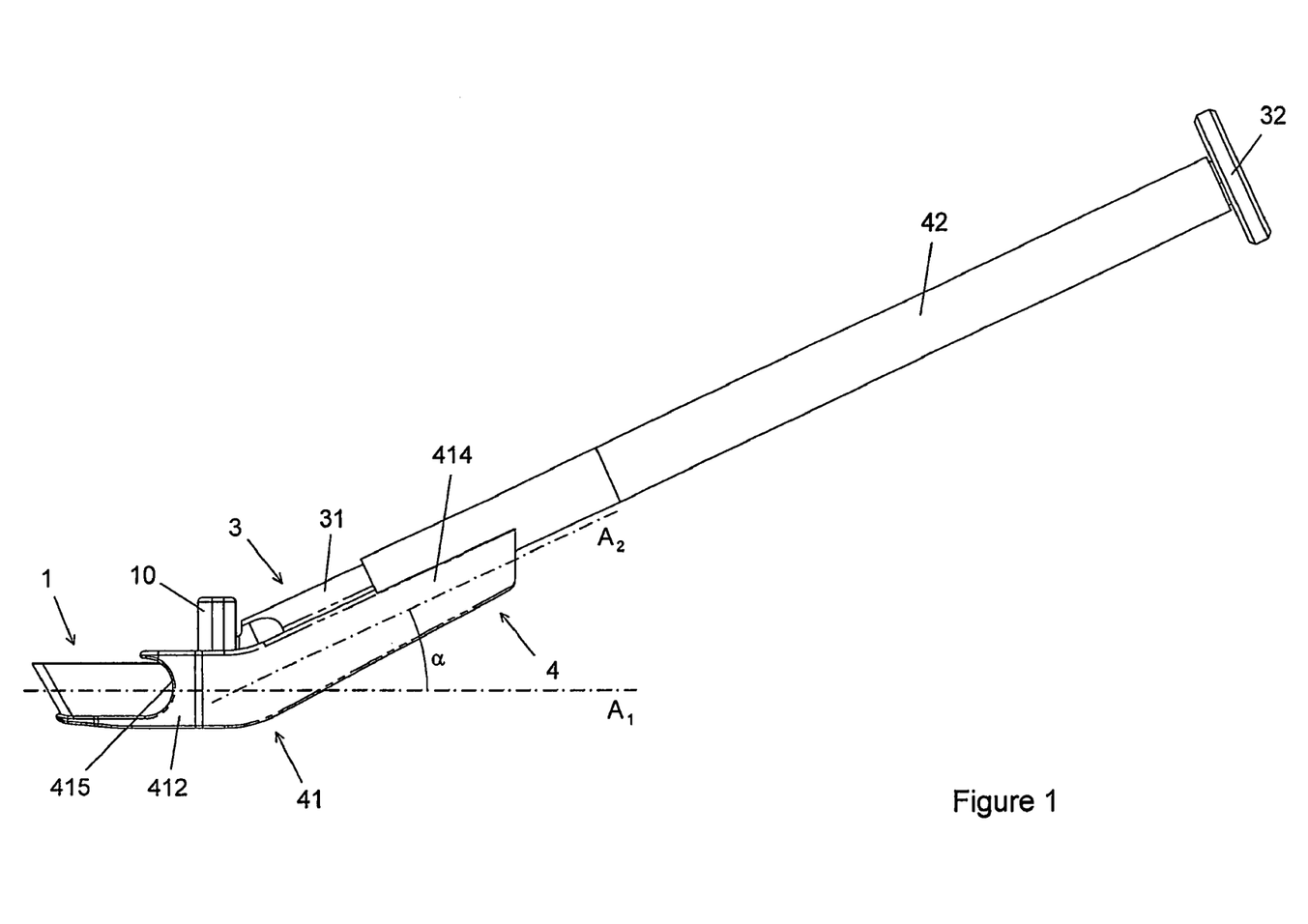
FIGS. 1 and 2 are a side view of the device according to the invention, the cutting element being respectively deployed and retracted.
Figure 2:
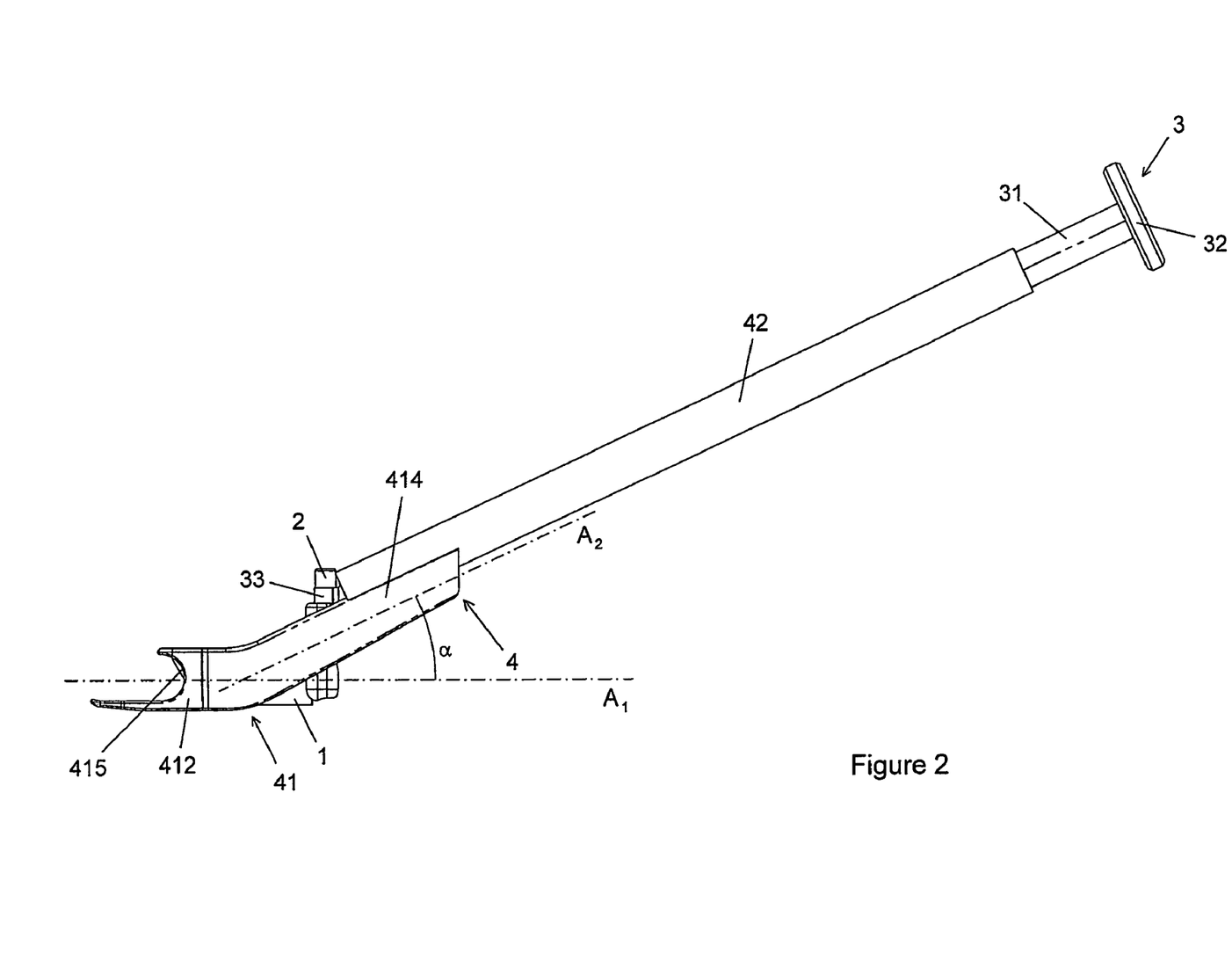
Figure 7:
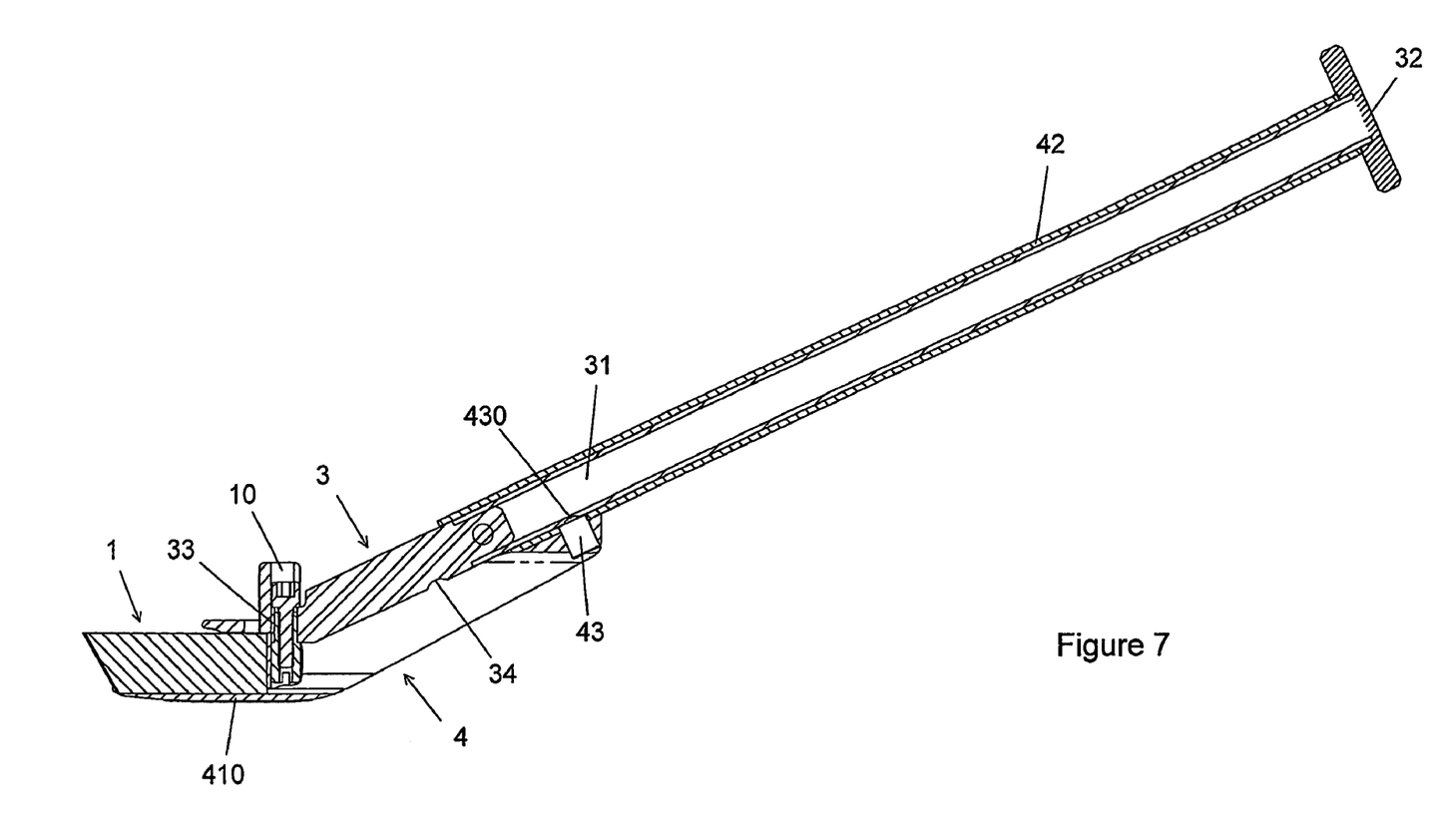
FIG. 7 is a cross-section view of the device according to the invention, along plane B-B of FIG. 6.
Figure 8:
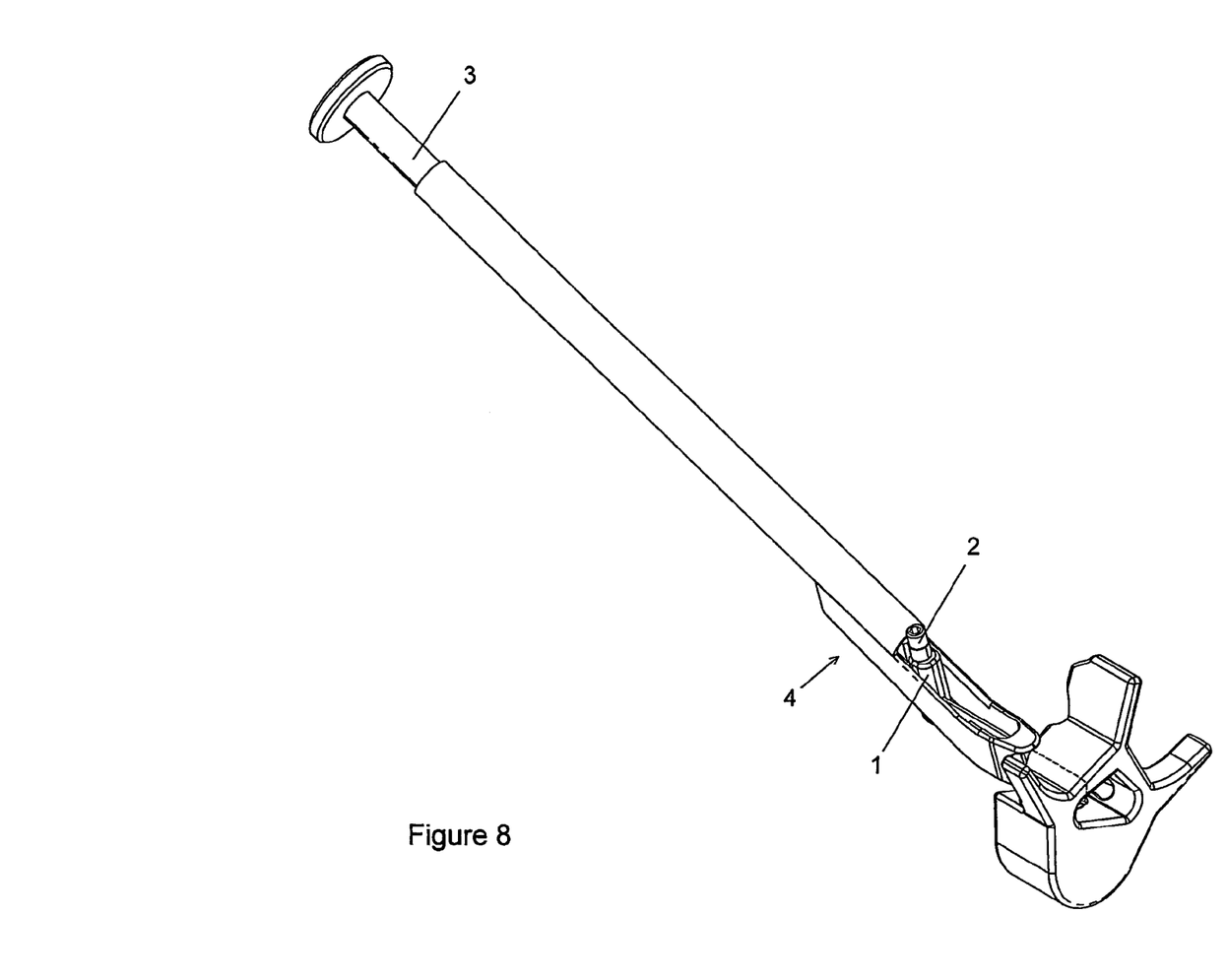
FIG. 8 is a perspective view of the device according to the invention, in position to section the vertebral lamina.

Side face portions 412 positioned at the front of the device according to the invention are provided with a recess 415, as can be seen in FIGS. 1 and 2 in particular, enabling the bottom part 410 of the base 4 of the device according to the invention to be caused to slide between the lamina to be sectioned and the dura mater as shown in FIG. 7. This recess 415 also acts as abutment for the vertebral lamina. When the vertebral lamina abuts recess 415 of the side face front portions 412, the bottom part 410 protrudes beyond the other side of the lamina, thereby providing full protection to the medullar canal when sectioning the lamina.

The second part 42 of the base 4 of the device according to the invention consists of a hollow tube formed at the end of the side face portions 414 with longitudinal axis $A_2$ that is opposite the intersection between the two side face portions 412, 414 and parallel to axis $A_2$.

To use the device according to the invention, it is assembled as follows. The device may be factory-assembled and can be easily re-assembled by an operator in particular if one of the parts of the device needs to be changed.

The sectioning means 1 of the device according to the invention are inserted on the bottom part 410 of the base 4, the cutting element 13 being oriented towards the front of the device. The second piston 3 is inserted in the hollow tube 42 of the base 4, its handle 32 being oriented towards the rear of the device so as to counter its weight effect, its handle 32 being larger than the diameter of the hollow tube 42, as can be seen in FIG. 1 in particular. The second piston 3 is made integral with the first piston 2, which is then inserted in the sleeve 10 of the sectioning means 1.

The assembly formed by the sectioning means 1, the first piston 2 and the second piston 3 is then able to slide in the base 4 of the device according to the invention between two end positions defined by abutments.

In the first end position, the abutment is formed by the handle 32 of the second piston 3 which bears against the rear end of the hollow tube 42 of the base 4 of the device. In this position, shown in particular in FIGS. 1, 6 and 7, the cutting element 13 of the sectioning means 1 reaches the front end of the bottom part 410 of the base 4 and the first piston 2 is at the bottom of the sleeve 10 of the sectioning means 1.

In the second end position, the abutment is formed by the screwhead 23 of the first piston 2 which bears against the front end of the hollow tube 42 of the base 4 of the device. In this position, shown in particular in FIGS. 2 and 5, the cutting element 13 is retracted between the side faces 412 of the base 4, as shown in FIG. 2 in particular giving a profile view of the device, and the rear of the sectioning means 1 no longer bears upon the bottom part 410 of the base 4 of the device. The longitudinal axis of the cutting element 13 is then retained substantially parallel to axis $A_1$ by means of a plate 413, formed substantially above the bottom part 410 of the base 4, this plate 413 being integral with side face portions 412 of longitudinal axis $A_1$. In this position, the upper end of the first piston 2 is positioned slightly outside the sleeve 10 of the sectioning means 1.

The second piston 3 close to the ring 33 comprises a slot (34, FIG. 7) complementary to the ball 430 of a ball stop 43 located at the rear of the first part 41 of the base 4. Therefore when the device according to the invention is in the second end position, this ball stop 43 holds it in this position. By exerting hand pressure on the handle of the second piston 3 it is possible to achieve easy release of the slot 34 from the ball 430.

To change from the first end position to the second end position, the device is operator-actuated. The hollow tube 42 of the base 4 of the device is held with one hand while the other hand pulls on the handle 32 of the second piston 3. In this manner, since the second piston 3 is integral with the first piston and since the second piston 3 slides parallel to axis $A_2$, the first piston 2 slides upwards parallel to the axis of the sleeve 10 of the sectioning means, and the sectioning means 1 slide towards the rear of the device parallel to axis $A_1$, which is perpendicular to the axis of the sleeve 10.

To section a vertebral lamina procedure is as follows. The operator places the device according to the invention in its second end position. The bottom part 410 of the base 4 of the device is then inserted between the laminas of two vertebrae and, helped by angle α of the base 4, the bottom part 410 of the base 4 is caused to slide between the lamina and the dura mater until the recess 415 of the side face front portion 412 of the base 4 abuts against the vertebral lamina to be sectioned. In this position, as shown in FIG. 7, a small portion of the bottom part 410 of the base 4 of the device projects beyond the other side of the vertebral lamina to be sectioned. The operator then holds the hollow tube 42 of the base 4 with one hand and with the other hand applies one or more sharp raps to cause lamina sectioning in the plane of the cutting element 13, over the entire thickness of the lamina. This operation is conducted with no risk to the spinal canal on account of bottom part 410 and recess 415.

This operation is repeated on the other side of the spinous process so as to remove the spinous process and free the medullar canal.

With this method, operating time is substantially reduced.

If necessary, surgery can be continued by sectioning the lamina of other vertebrae. In this case, with the sectioning device of the invention, the time saved soon becomes considerable.

Angle α lying between the sliding axis of the cutting element 13 and the sliding axis $A_2$ of the second piston 3 may vary according to patient weight and to the part of the spine concerned by lamina sectioning. It is therefore useful for operators to have a plurality of bases of sectioning devices according to the invention, each having a different angle α to adapt to the case being treated.

Also, the sectioning means 1 are interchangeable. Therefore when the cutting element 13 of the sectioning means 1 is worn, only the sectioning means 1 need to be changed, the other elements of the sectioning device of the invention being maintained.

It will be obvious to persons skilled in the art that the present invention allows embodiments in numerous other specific forms without departing from the sphere of application of the invention as claimed. Therefore, the above embodiments must be considered as illustrative but can be modified within the area defined by the scope of the appended claims, and the invention is not to be restricted to the details given above.

The invention claimed is:

1. A device for sectioning a vertebral lamina comprising:
   a longitudinal plane of the device and first, second, and third axes, none of which axes are parallel or collinear and all of which axes lie in the longitudinal plane of the device;
   a base adapted to position the device and protect the medullar canal when sectioning the lamina;
   a sectioning component mounted in the base and adapted to slide linearly along the first axis, the sectioning component comprising a sleeve through which passes the second axis and a cutting element distal from the sleeve and lying within the longitudinal plane of the device;
   a first piston mounted in the sleeve with a longitudinal axis of the first piston adapted to slide linearly in the sleeve along the second axis, which sliding induces linear sliding of the sectioning component in the base along the first axis; and
   a second piston attached to the first piston opposite the sectioning component and adapted to slide linearly in the base along the third axis, which sliding induces linear sliding of the first piston in the sleeve along the second axis.

2. Sectioning device according to claim 1, in which the second piston comprises a body provided, at one of its ends, with a ring into which the first piston engages, the ring being held on the first piston by a screwhead and, at the other of its ends, with a handle, the body being slide-mounted in a tube of the base of the device, and the handle being sized larger than the tube diameter.

3. Sectioning device according to claim 2, in which the base further comprises:
   a bottom part in which the sectioning component slides, the bottom part having a rail in which the cutting element slides; and
   two adjacent side faces, each side face comprising a first portion having a longitudinal axis parallel to the first axis and a second portion having a longitudinal axis parallel to the third axis.

4. Sectioning device according to claim 3, in which the tube extends from the second portions of the side faces.

5. Sectioning device according to claim 4, in which the bottom part opposite the tube has a tapered portion, and the first portions of the side faces each comprises a recess arranged to permit sliding of the tapered portion between adjacent vertebrae and abutting of the device against the lamina to be sectioned.

6. Sectioning device according to any one of claims 1-5, in which the cutting element has an end beveled to facilitate sectioning of the vertebral lamina.

\* \* \* \* \*